United States Patent
Senetar et al.

(10) Patent No.: US 11,053,183 B1
(45) Date of Patent: Jul. 6, 2021

(54) PROCESS AND APPARATUS FOR SEPARATING METHANOL FROM OTHER OXYGENATES

(71) Applicant: UOP LLC, Des Plaines, IL (US)

(72) Inventors: John J. Senetar, Naperville, IL (US); Yogesh Kumar Gupta, Gurgaon (IN); Joseph A. Montalbano, Elmhurst, IL (US)

(73) Assignee: UOP LLC

( * ) Notice: Subject to any disclaimer, the term of this patent is extended or adjusted under 35 U.S.C. 154(b) by 0 days.

(21) Appl. No.: 16/805,431

(22) Filed: Feb. 28, 2020

(51) Int. Cl.
*C07C 29/84* (2006.01)
*B01D 3/14* (2006.01)
*B01D 3/40* (2006.01)
*C07C 29/10* (2006.01)

(52) U.S. Cl.
CPC .............. *C07C 29/84* (2013.01); *B01D 3/143* (2013.01); *B01D 3/40* (2013.01); *C07C 29/10* (2013.01)

(58) Field of Classification Search
CPC ......... C07C 29/80; C07C 29/82; C07C 29/84; C07C 29/86
See application file for complete search history.

(56) References Cited

U.S. PATENT DOCUMENTS

| | | | |
|---|---|---|---|
| 4,544,776 A | 10/1985 | Osterburg et al. | |
| 5,863,391 A * | 1/1999 | Rueter | C07C 29/80 203/14 |
| 7,692,031 B2 * | 4/2010 | Goebbel | C07D 301/32 549/541 |
| 2004/0215043 A1 | 10/2004 | Senetar | |
| 2008/0161616 A1 | 7/2008 | Miller | |

FOREIGN PATENT DOCUMENTS

| | | |
|---|---|---|
| EP | 2338864 A1 | 6/2011 |
| WO | 2005017071 A1 | 2/2005 |
| WO | 2015199825 A1 | 12/2015 |

OTHER PUBLICATIONS

ISA, "Search Report and Written Opinion of ISA for PCT/US2021/019651 dated May 13, 2021".

* cited by examiner

*Primary Examiner* — Medhanit W Bahta
(74) *Attorney, Agent, or Firm* — Paschall & Associates, LLC; James C. Paschall

(57) ABSTRACT

We have discovered that addition of water to a mixture of oxygenates increases their volatility relative to methanol. A process and apparatus are disclosed for separating methanol from other oxygenates. Water is separated from a stream comprising water, methanol and at least one other oxygenate to provide a water rich stream and a methanol and oxygenate rich stream. The methanol and oxygenate rich stream and water are fed to a column to provide an oxygenate rich stream and a methanol and water extract stream. The methanol and water can then be readily separated from each other.

14 Claims, 1 Drawing Sheet

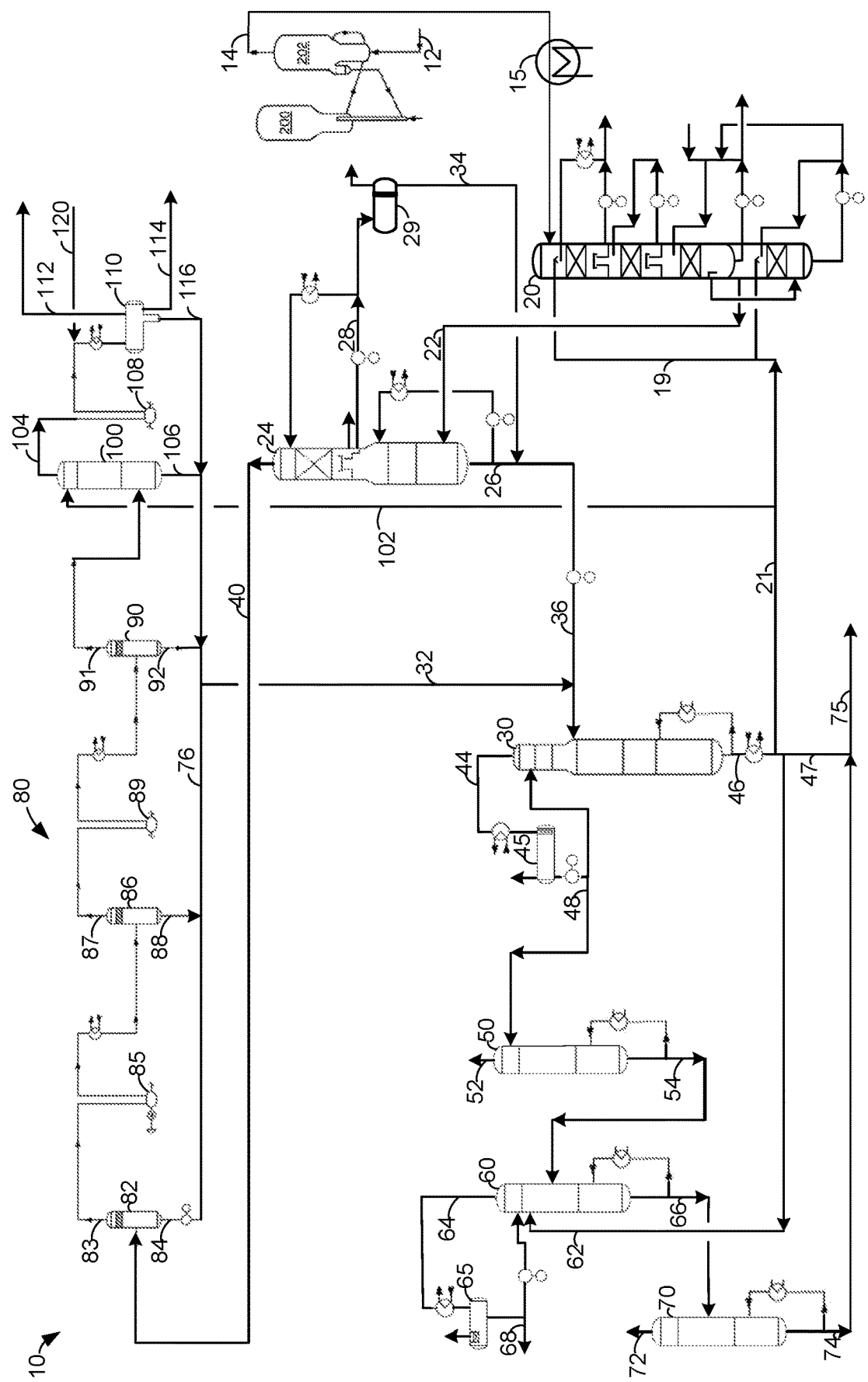

PROCESS AND APPARATUS FOR SEPARATING METHANOL FROM OTHER OXYGENATES

FIELD

The field is the separation of methanol from other oxygenates particularly in the presence of water.

BACKGROUND

A major portion of the worldwide petrochemical industry is involved with the production of light olefin materials and their subsequent use in the production of numerous important chemical products. Such production and use of light olefin materials may involve various well-known chemical reactions including, for example, polymerization, oligomerization, and alkylation reactions. Light olefins generally include ethylene, propylene and mixtures thereof. These light olefins are essential building blocks used in the modern petrochemical and chemical industries. A major source for light olefins in present day refining is the steam cracking of petroleum feeds. For various reasons, sources other than petroleum are sought for the massive quantities of raw materials that are needed to supply the demand for these light olefin materials.

The search for alternative materials for light olefin production has led to the use of oxygenates such as alcohols and, more particularly, to the use of methanol, ethanol, and higher alcohols or their derivatives or other oxygenates such as dimethyl ether (DME) and diethyl ether, for example. Molecular sieves such as microporous crystalline zeolite and non-zeolitic catalysts, particularly silicoaluminophosphates (SAPO), are known to promote the conversion of oxygenates to hydrocarbon mixtures, particularly hydrocarbon mixtures composed largely of light olefins. This process has been termed, the oxygenate-to-olefins (OTO) process and also the methanol-to-olefins (MTO) process.

Such processing, wherein the oxygenate-containing feed is primarily methanol or a methanol-water combination, typically results in the release of significant quantities of water upon the sought conversion of such feeds to light olefins. For example, such processing normally involves the release of about 2 mols of water per mol of ethylene formed and the release of about 3 mols of water per mol of propylene formed.

The methanol to olefins process reaction conditions are selected such that the overall oxygenate feed conversion is high, over 97%; nevertheless, there remains unconverted reactants which exit the reactor as methanol and DME. In order to achieve overall high yields for the process, it is necessary to recover the unconverted methanol and DME feed for recycle to the MTO reactor. In addition to olefins, the MTO process also generates a number of other oxygenate byproducts, most notably acetone, acetaldehyde and methyl ethyl ketone. Conventional means used to recover and recycle methanol and DME also result in recycling of the oxygenate byproducts.

These oxygenate byproducts do not readily convert over MTO catalyst when recycled, and as a result these byproducts could build up in the recycle streams. The high concentrations of these oxygenate byproducts in the recycle streams could lead to operational difficulties and require greater capacity to recover and recycle them to the reactor with no advantage.

Processes and equipment are sought to separate reactant oxygenates from byproduct oxygenates.

BRIEF SUMMARY

We have discovered that addition of water to a mixture of oxygenates increases their volatility relative to methanol. A process and apparatus are disclosed for separating methanol from other oxygenates. Water is separated from a stream comprising water, methanol and at least one other oxygenate to provide a water rich stream and a methanol and oxygenate rich stream. The methanol and oxygenate rich stream and water are fed to a column to provide an oxygenate rich stream and a methanol and water extract stream. The methanol and water can then be readily separated from each other.

Additional details and embodiments of the disclosure will become apparent from the following detailed description.

BRIEF DESCRIPTION OF THE DRAWINGS

The FIGURE is a schematic view of a disclosed process and apparatus.

DETAILED DESCRIPTION

DME has a volatility near that of propane and is therefore easily separated from unreacted methanol and oxygenate byproducts. However, oxygenate byproducts such as acetone, acetaldehyde, and methyl ethyl ketone (MEK) have a volatility close to that of methanol, thereby making separation from methanol difficult. We found surprisingly that the addition of dilution water increases the volatility of acetone, acetaldehyde and MEK relative to methanol.

The primary separation of olefin product from water generates a water stream that contains unreacted methanol, and other oxygenate byproducts; such as acetone, acetaldehyde, and MEK. A distillation column separates a water bottoms stream that is substantially free of methanol and oxygenate byproducts and an overhead stream comprising most of the methanol and oxygenate byproducts. The overhead stream is then sent to a second distillation column to separate the oxygenate byproducts from the unreacted methanol. In this second distillation column, stripped water from the first distillation column may be introduced at the top of the second distillation column so as to facilitate the separation of the oxygenate byproducts from methanol. The addition of water to the second distillation column enables the separation of methanol from the byproduct oxygenate impurities. The initial water separation is required to concentrate the hydrocarbon oxygenates to make them susceptible to volatility enhancement by the addition of dilution water.

As used herein, oxygenates typically means hydrocarbon oxygenates to distinguish them from water, which can be termed an oxygenate.

The term "column" means a distillation column or columns for separating one or more components of different volatilities. Unless otherwise indicated, each column includes a condenser on an overhead of the column to condense and reflux a portion of an overhead stream back to the top of the column and a reboiler at a bottom of the column to vaporize and send a portion of a bottoms stream back to the bottom of the column. Feeds to the columns may be preheated. The top pressure is the pressure of the overhead vapor at the vapor outlet of the column. The bottom temperature is the liquid bottom outlet temperature. Overhead lines and bottoms lines refer to the net lines from the column downstream of any reflux or reboil to the column. Stripping columns may omit a reboiler at a bottom of the column and instead provide heating requirements and separation impetus from a fluidized inert media such as steam. Stripping columns typically feed a top tray and take main product from the bottom.

The present disclosure of oxygenate separation may be used in an oxygenate to olefin process such as an MTO process and apparatus, but it may be used in other contexts. However, the process and apparatus will be described herein in the context of an MTO process and apparatus 10.

Turning to the FIGURE of a process and apparatus 10, a superheated feed stream in line 12 is fed to an oxygenate conversion reactor 202 that reacts an oxygenate such as methanol or DME with fluidized catalyst. A hot vaporous reactor effluent stream in line 14 is withdrawn from an oxygenate conversion reactor 202 which periodically or continuously circulates fluidized catalyst in a conventional manner to the regeneration zone 200 to maintain the selectivity and the conversion desired. Reactor 202 is maintained at effective conditions for the conversion of the oxygenate to produce light olefin products and generate oxygenated byproducts. The hot vaporous reactor effluent stream may comprise light olefins, water, and oxygenates.

The hot vaporous reactor effluent stream in line 14 may be preliminarily cooled in a reactor effluent heat exchanger 15 to recover heat before it is passed to a quench tower 20. In the quench tower 20, the vaporous reactor effluent is desuperheated, neutralized of organic acids and clarified of catalyst fines by direct contact with a water stream supplied in line 19 which may be taken from a stripped water stream in line 21. A quenched reactor effluent stream in line 22 is discharged from the quench tower 20 and fed to a product separator column 24. The product separator column 24 may be in downstream communication with the MTO reactor 202.

The product separator 20 comprises two sections for separating the reactor effluent stream into a product olefin stream in an overhead line 40, an intermediate liquid stream in an intermediate line 28 and a water stream in a bottoms line 26. A first, or lower, section receives the quenched reactor effluent stream in line 22. In the lower section, most of the heat is removed from the quenched reactor effluent stream while partially condensing the water in the quenched reactor effluent stream to generate a product water stream in bottoms line 26 comprising a portion of the oxygenate byproducts in the quenched reactor effluent stream in line 22. A portion of the product water stream is cooled and pumped around to the top of the first section of the product separator 24 to cool the quenched reactor effluent stream in line 22. A second portion of the second bottoms stream 26 is passed to a water stripper column 30. A water return stream comprising oxygenate byproducts from the compression section 80 in return line 32 can also be passed to the water stripper column 30. The water stripper column 30 may be in downstream communication with the product separator column 24.

A vapor stream from the first section of the product separator 24 is passed to the second, or upper, section of the product separator. An intermediate stream in line 28 comprising hydrocarbons, oxygenate byproducts, and water in liquid phase is withdrawn at a bottom of the upper section. A portion of the intermediate stream in line 28 is cooled and passed as reflux to the top of the second section of the product separator 24. The remainder of the intermediate stream in line 28 is passed to a coalescer 29 to separate a hydrocarbon overhead stream from an aqueous stream in line 34 which is fed back to the product water stream and pumped to the water stripper column 30 in line 36. An overhead product stream comprising olefins from the product separator column in line 40 may be delivered to the compression section 80.

The product water stream in the line 36 includes dilute hydrocarbon oxygenates such as DME, methanol, acetaldehyde, acetone and MEK. The water stripper column 30 separates or strips the oxygenates into a methanol and oxygenate rich stream in an overhead line 44 rich in both methanol and at least another oxygenate and a water rich stream in a bottoms line 46. As used herein, the term "a component-rich stream" means that the rich stream coming out of a vessel has a greater concentration of the component than the feed to the vessel and preferably than all other streams withdrawn from the vessel. As used herein, the term "a component-lean stream" means that the lean stream coming out of a vessel has a smaller concentration of the component than the feed to the vessel and preferably than all other streams withdrawn from the vessel.

A portion of the water rich stream in the bottoms line is reboiled and returned to the water stripping column 30. A net water rich stream in the bottoms line 46 can be divided into an extractant stream provided in line 62 to an extractive distillation column 60, a water rich stream in the remaining bottoms line 47 and a stripped water supply stream in water supply line 21 fed to the quench column 20 in line 19 and the oxygenate absorber in line 102. The oxygenate rich stream in the overhead line 44 may be cooled and partially condensed and fed to a receiver separator 45. As used herein, the term "separator" means a vessel which has an inlet and at least an overhead vapor outlet and a bottoms liquid outlet and may also have an aqueous stream outlet from a boot.

Uncondensed light hydrocarbons can be purged from a receiver overhead line while a hydrocarbon lean, methanol and oxygenate rich stream can be removed in a bottoms line 48 and comprise methanol, DME, acetaldehyde, acetone and MEK. A portion of the hydrocarbon lean, methanol and oxygenate rich stream can be returned to the water stripper column 30 as reflux.

In one embodiment the water stripper column 30 temperature may be about 115° C. (239° F.) to about 150° C. (302° F.) at the bottom of the water stripper column and the pressure may be about 75 kPa gauge (11 psig) to about 345 kPa (50 psig) at the top of the water stripper column.

The term "communication" means that fluid flow is operatively permitted between enumerated components, which may be characterized as "fluid communication". The term "downstream communication" means that at least a portion of fluid flowing to the subject in downstream communication may operatively flow from the object with which it fluidly communicates.

The hydrocarbon lean, methanol and oxygenate rich stream may be fed to an extractive distillation column 60 to separate methanol from at least one other oxygenate. However, the hydrocarbon lean, methanol and oxygenate rich stream comprises DME which easily separates from methanol. Hence, the hydrocarbon lean, methanol and oxygenate rich stream may be fed to a DME stripper column 50 to easily remove the DME. The DME stripper column 50 may be in downstream communication with the water stripper column 30. The DME stripper column 50 may separate or strip DME into a DME rich stream in an overhead line 52 and provide a DME lean, methanol and oxygenate rich stream in a bottoms line 54. The DME rich stream in the overhead lien 52 may be recycled to the MTO reactor 202 as reactant feed. A portion of the DME lean, methanol and oxygenate rich stream may be reboiled and recycled to the DME stripper column 50. The net, DME lean, methanol and oxygenate rich stream in bottoms line 54 may be fed to the extractive distillation column 60. The extractive distillation column 60 may be in downstream communication with the water stripper column 30 and upstream of any communication with the product separator column 24 to assure that no inert oxygenates build up in the compression section 60 without an avenue for return to the water stripper column 30. Additionally, in an embodiment, the extractive distillation column may be in downstream communication with the DME stripper column 50.

In one embodiment the DME stripper column 50 temperature may be about 85° C. (185° F.) to about 120° C. (248° F.) at the bottom of the DME striper column and the pressure may be about 75 kPa gauge (11 psig) to about 414 kPa (60 psig) at the top of the column. The DME stripper column 50 may utilize an overhead condenser and receiver separator in addition to or instead of the overhead condenser and receiver 45 for the water stripper column 30 to remove a light hydrocarbon purge. The DME stripper overhead can be recycled to MTO reactor 202.

The DME lean, methanol and oxygenate rich stream may be fed to a distillation column to separate methanol from at least one other hydrocarbon oxygenate and preferably all other hydrocarbon oxygenates. The separation would be difficult because the other hydrocarbon oxygenates have volatilities relative to methanol that are small. However, we have found that the addition of water increases the volatility of hydrocarbon oxygenates acetaldehyde, acetone and MEK relative to methanol while slightly reducing the still high relative volatility of DME to methanol. Hence, one alternative is to remove DME before the addition of water as just described.

In an aspect, methanol is separated from an initial mixture of oxygenates including water, methanol and at least one other hydrocarbon oxygenate such as acetaldehyde, acetone or MEK. Bulk water may be separated from the initial mixture to provide a water lean mixture comprising methanol and said at least one other oxygenate. It is necessary to remove the bulk water to concentrate the oxygenates in the initial mixture. DME may be separated from the water lean mixture to provide a water and DME lean mixture. Water is then added to the water lean mixture comprising methanol and the at least one other oxygenate to provide a water enriched mixture which enhances the volatilities of the at least one other oxygenate relative to methanol. The added water may be taken from the bulk water initially removed from the initial mixture. Methanol and water are then more easily extracted from the at least one other oxygenate in the water enriched mixture.

Translated to the process and apparatus 10, the DME lean, methanol and oxygenate rich stream in the net bottoms line 54 may be fed to an extractive distillation column 60 to separate methanol from at least one other hydrocarbon oxygenate and preferably all other hydrocarbon oxygenates. An extractant stream of water may also be fed to the extractive distillation column 60 at a location, such as at the top quarter of the column, above a location, such as the middle quarter of the column, at which the DME lean, methanol and oxygenate rich stream is fed to the column. The extractant stream may be provided in line 62 which may be taken from the water rich stream in the water stripper bottoms line 46.

The flow rate of the extractant stream of water to the extractive distillation column 60 should be 1.5 to about 3 times that of the flow rate of hydrocarbon oxygenates to the extractive distillation column 60 in the DME lean, methanol and oxygenate rich stream and 1 to about 3 times the flow rate of the entire DME, lean, methanol and oxygenate rich stream may will also comprise substantial water.

The extractive distillation column 60 produces an oxygenate rich stream in an overhead line 64 comprising the at least one other hydrocarbon oxygenate, such as acetone, acetaldehyde, MEK and DME and a methanol and water rich extract stream in a bottoms line 66. A portion of the methanol and water rich stream in the bottoms line 66 may be reboiled and returned to the extractive distillation column 60. The oxygenate rich stream in the overhead line 64 may be cooled and partially condensed and fed to a receiver separator 65. Uncondensed light hydrocarbons can be purged from a receiver overhead line while a hydrocarbon lean oxygenate rich stream can be removed in a receiver bottoms line 68 and comprise DME, acetaldehyde, acetone and MEK. A portion of the hydrocarbon lean oxygenate rich stream can be returned to the extractive distillation column 60 as reflux at a location above the location at which the extractant stream is added to the extractive distillation column 60. The light hydrocarbon purge(s) may be fed to light olefin recovery.

At least 99 wt %, and preferably at least 99.5 wt %, of the hydrocarbon oxygenates other than methanol fed to the extractive distillation column 60 may be recovered in the oxygenate rich stream in the overhead line 64 of the extractive distillation column 60 and the hydrocarbon lean, oxygenate rich stream in the bottoms line 68 of the extraction receiver 65. At least 90 wt %, and preferably at least 95 wt %, of the methanol may be recovered in the methanol and water rich stream in the net bottoms line 66.

The extractive distillation column 60 may have operating conditions including a bottoms temperature in the range of about 75° C. (167° F.) to about 150° C. (302° F.) and an overhead pressure in the range of about 75 kPa gauge (11 psig) to about 200 kPa gauge (29 psig). The extractive distillation column 60 may be in downstream communication with the overhead line 44 of the water stripper column 30 and with a bottoms line 46 of said water stripper column.

The recovered methanol is an MTO reactant that can be recycled to the MTO reactor 202, but it is not desirable to recycle the water with the methanol. Hence, the methanol and water rich stream in the net bottoms line 66 may be fed to a methanol stripper column 70 to separate a methanol rich stream in an overhead line 72 from a final water rich stream in a bottoms line 74. The methanol rich stream in the overhead line 72 may then be recycled to the MTO reactor 202 without inert oxygenates that do not react and can otherwise build up in the process and apparatus 10. A portion of the final water rich stream in the bottoms line 74 may be reboiled and recycled to the methanol stripper column 70. The final water rich stream in the net bottoms line 74 may be forwarded to water treatment in line 75 along with an unrecycled portion of the water rich stream in the remaining bottoms line 47 from the water stripper bottoms line 46.

The product olefin stream back in the product overhead line 40 carries valuable olefinic products which must be recovered. The compression section 80 increases the pressure of the product olefin stream necessary for downstream processing such as used in conventional light olefin recovery units. The compression section 80 may comprise a first knock out drum 82 which separates the product olefin stream into a pressurized first olefin rich stream in an overhead line 83 and a first aqueous stream rich in oxygenates in a bottoms line 84. The olefin rich stream in the overhead line 83 may be fed to a compressor 85, cooled and directed to a second knockout drum 86. The aqueous stream in the bottoms line 84 is pumped via a manifold line 76 to the return line 32 which returns the water stream with the product water stream in the separator bottoms line 36 to the water stripper column 30.

The compression section 80 may comprise a second knock out drum 86 which separates the pressurized first olefin rich stream into a second pressurized olefin rich stream in an overhead line 87 and a second aqueous stream rich in oxygenates in a bottoms line 88. The second olefin rich stream in the overhead line 87 may be fed to a compressor 89, cooled and directed to a third knockout drum 90. The aqueous stream in the bottoms line 88 is pumped to the return line 32 via the manifold line 76 which returns the water stream with the product water stream in the separator bottoms line 36 to the water stripper column 30.

The compression section 80 may comprise a third knock out drum 90 which separates the pressurized second olefin rich stream into a third pressurized olefin rich stream in an overhead line 91 and a third aqueous stream rich in oxygenates in a bottoms line 92. The third olefin rich stream in the overhead line 91 may be fed to the oxygenate absorber column 100. The aqueous stream in the bottoms line 92 is pumped to the return line 32 via manifold line 76 which returns the water stream with the product water stream in the separator bottoms line 36 to the water stripper column 30.

Types of suitable compressors may include centrifugal, positive displacement, piston, diaphragm, screw, and the like. In one embodiment, the compressors 85, 89 in the compression section 80 are centrifugal compressors. The final discharge pressure can be between about 1,000 kPa gauge (145 psig) and about 2,000 kPa gauge (290 psig). The compressor discharge may be cooled to about ambient temperatures using conventional heat transfer methods.

As illustrated in the FIGURE and according to a preferred embodiment, at least a portion of the compressed product stream via the overhead line 91 is contacted in the oxygenate absorber column 100 at effective conditions to absorb at least a quantity of effluent oxygenates with a cooled lean water stream introduced via a line 102 and taken from the water rich stream in the water stripper bottoms line 46 with no water taken directly from the product separator column 20 without prior removal of oxygenates. The contacting in the oxygenate absorber column 100 produces an absorption olefin rich stream in the overhead line 104 and an absorption water rich stream in a bottoms line 106 comprising a quantity of effluent oxygenates. The absorption olefin rich stream in the overhead line 104 may be fed to a third compressor 108, partially condensed by cooling and fed to an absorber separator 110. A stream from an olefin recovery section in line 120 may be fed to the absorber separator 110 with the compressed absorption olefin rich stream in line 104. The absorption water rich stream in the bottoms line 106 may be fed to the return line 32 via the manifold line 76 which returns the water stream with the product water stream in the separator bottoms line 36 to the water stripper column 30.

The oxygenate absorber 100 may have operating conditions including a bottoms temperature range of about 30° C. (86° F.) to about 50° C. (122° F.) and an overhead pressure range of about 1,500 kPa gauge (217 psig) to about 2,000 kPa gauge (290 psig).

The absorber separator 110 separates the pressurized absorption olefin rich stream into a light gas stream in line 112 which may be fed to a scrubber for acid gas removal, a condensed absorption olefin rich stream in a bottoms line 114 which may be forwarded to olefin recovery and an aqueous boot stream in boot line 116. The aqueous boot stream in the boot line 116 may be pumped to the return line 32 via the manifold line 76 which returns the aqueous boot stream with the product water stream in the separator bottoms line 36 to the water stripper column 30.

The process and apparatus 10 provide recovery of reactant oxygenates for recycle to the MTO reactor 202 without recycling inert oxygenates to reactor which will build up in the system with no means of recovery. This is achieved by removing inert oxygenates from reactive oxygenates in the water stream before recycling to the MTO reactor 202. Additionally, adding water back to the inert oxygenates improves and facilitates their separation from the reactant oxygenate, methanol.

EXAMPLE

Relative volatilities were calculated for a mixture of methanol with substantial water and small fractions of hydrocarbon oxygenates and then recalculated for the same mixture but with diluted with more water than methanol at 0.45 MPa and 43.3° C. Results are shown in Table 1. K value is the ratio of mole fraction in the vapor phase to the mole fraction in the liquid phase, often referred to as "y/x".

TABLE 1

| | Without Extra Water Addition | | | With Extra Water Addition | | | |
|---|---|---|---|---|---|---|---|
| Component | wt % | K value | Oxygenate Relative Volatility to Methanol | wt % | K value | Oxygenate Relative Volatility to Methanol | Difference Increase in Relative Volatility, % |
| Water | 0.39 | 0.02 | — | 0.73 | 0.04 | — | — |
| Methanol | 0.51 | 0.11 | 1.0 | 0.22 | 0.28 | 1.0 | — |
| DME | 0.04 | 9.83 | 93.5 | 0.02 | 19.49 | 69.53 | −25.60 |
| Acetaldehyde | 0.02 | 0.59 | 5.6 | 0.01 | 3.11 | 11.10 | 98.74 |
| Acetone | 0.04 | 0.39 | 3.7 | 0.02 | 1.30 | 4.62 | 25.82 |
| MEK | 0.01 | 0.31 | 3.0 | 0.01 | 1.90 | 6.76 | 128.67 |

Addition of dilution water increases the relative volatility of acetaldehyde, acetone, and MEK compared to methanol thereby making their separation from methanol easier. The relative volatility of DME to methanol is negatively impacted by water dilution. However, the relative volatility of DME to methanol is still very high and does not present any challenge for separation particularly compared to the advantage obtained in the increased relative volatilities of the other hydrocarbon oxygenates.

We simulated operation of a water stripper column with 30 ideal stages and a feed stage 15 stages from the top. The reflux rate was 15,440 kg/h and with an overhead pressure of 329 kPa (gauge) (48 psig) and a bottoms temperature of 134° C. (273° F.). Reboiler duty was 23.2 GJ/h and the condenser duty was −15.2 GJ/h. In the second simulation, 14,875.9 additional water was added to the top stage of the column. Results with and without water addition are given in Table 2.

TABLE 2

|  | Without Extra Water Feed to Top Tray | | | | With Extra Water to Top Tray | | | |
|---|---|---|---|---|---|---|---|---|
|  | Feed | Bottoms | Distillate Liquid | Distillate Vapor | Feed | Bottoms | Distillate Liquid | Distillate Vapor |
| Components | kg/h | kg/h | kg/h | kg/h | kg/h | kg/h | kg/h | kg/h |
| Water | 4823.7 | 4823.6 | 0.1 | 0 | 4823.7 | 20517 | 180.6 | 2 |
| Methanol | 6348 | 6083.9 | 259.8 | 4.3 | 6348 | 6067.6 | 273.3 | 7 |
| DME | 447.5 | 0 | 292.2 | 155.3 | 447.5 | 0 | 276.3 | 171.2 |
| Acetaldehyde | 221.9 | 0.1 | 209.6 | 12.2 | 221.9 | 0 | 198.2 | 23.7 |
| Acetone | 472.1 | 1.4 | 459.7 | 11 | 472.1 | 0.003 | 452 | 20.1 |
| MEK | 143.3 | 141.2 | 2 | 0 | 143.3 | 0.0128 | 140.1 | 3.2 |
| Additional Water to Top Tray | 0 | | | | 15875.896 | | | |
| Methanol Recovery in Bottoms, wt % | 95.84 | | | | 95.58 | | | |
| Oxygenate Recovery in Overhead, wt % | 88.89 | | | | 100 | | | |

The additional dilution water to the extractive distillation column vastly reduces hydrocarbon oxygenate in the bottoms stream except for methanol which is the component desired for separation in the bottoms. Most of the methanol still exits in the bottoms with water while virtually all other hydrocarbon oxygenates exit in the overhead stream. The addition of dilution water enables recovery of at least 99.7 wt % hydrocarbon oxygenates from methanol in the overhead and recovery of at least 95% of methanol reactant in the bottoms. The simple addition of dilution water to the separation unexpectedly produced astounding results.

SPECIFIC EMBODIMENTS

While the following is described in conjunction with specific embodiments, it will be understood that this description is intended to illustrate and not limit the scope of the preceding description and the appended claims.

A first embodiment of the invention is a process for separating methanol from other oxygenates comprising separating water from a stream comprising water, methanol and at least one other oxygenate to provide a water rich stream and a methanol and oxygenate rich stream; feeding the methanol and oxygenate rich stream and water to an extractive distillation column to provide an oxygenate rich stream and a methanol and water extract stream. An embodiment of the invention is one, any or all of prior embodiments in this paragraph up through the first embodiment in this paragraph wherein the at least one other oxygenate includes dimethyl ether and further comprising separating dimethyl ether from the oxygenate rich stream to provide a dimethyl ether rich stream and a dimethyl ether lean, methanol and oxygenate rich stream and feeding the DME lean, methanol and oxygenate rich stream to the extractive distillation column. An embodiment of the invention is one, any or all of prior embodiments in this paragraph up through the first embodiment in this paragraph further comprising feeding the dimethyl ether rich stream to an oxygenate conversion reactor. An embodiment of the invention is one, any or all of prior embodiments in this paragraph up through the first embodiment in this paragraph wherein the water, fed to the extractive distillation column, is taken from the water rich stream. An embodiment of the invention is one, any or all of prior embodiments in this paragraph up through the first embodiment in this paragraph further comprising separating methanol from the water to provide a water rich stream and a methanol rich stream. An embodiment of the invention is one, any or all of prior embodiments in this paragraph up through the first embodiment in this paragraph further comprising feeding the methanol rich stream to an oxygenate conversion reactor. An embodiment of the invention is one, any or all of prior embodiments in this paragraph up through the first embodiment in this paragraph wherein the mixture of water, methanol and at least one other oxygenate also includes light hydrocarbons and further comprising separating the light hydrocarbons from the methanol and oxygenate rich stream. An embodiment of the invention is one, any or all of prior embodiments in this paragraph up through the first embodiment in this paragraph wherein the mixture of water, methanol and at least one other oxygenate also includes light hydrocarbons and further comprising separating the light hydrocarbons from the oxygenate rich stream. An embodiment of the invention is one, any or all of prior embodiments in this paragraph up through the first embodiment in this paragraph wherein the other oxygenate comprises one of acetaldehyde, acetone and methyl ethyl ketone. An embodiment of the invention is one, any or all of prior embodiments in this paragraph up through the first embodiment in this paragraph wherein the water in the extractive distillation column increases the volatility of the other oxygenates relative to methanol. An embodiment of the invention is one, any or all of prior embodiments in this paragraph up through the first embodiment in this paragraph wherein the stream comprising water, methanol and at least one other oxygenate is provided by a product separator column bottoms stream. An embodiment of the invention is one, any or all of prior embodiments in this paragraph up through the first embodiment in this paragraph wherein the stream comprising water, methanol and at least one other oxygenate is provided by an oxygenate absorber column bottoms stream.

A second embodiment of the invention is an apparatus for recovering oxygenates comprising a product separator column in downstream communication with an MTO reactor; a water stripper column in downstream communication with the product separator column; an extractive distillation column in downstream communication with the water stripper column upstream of any communication with the product separator column. An embodiment of the invention is one, any or all of prior embodiments in this paragraph up through the second embodiment in this paragraph further comprising a DME stripper column in downstream communication with the water stripper column and the extractive distillation column is in downstream communication with the DME stripper column. An embodiment of the invention is one, any or all of prior embodiments in this paragraph up through the second embodiment in this paragraph wherein the extractive distillation column is in downstream communication with an overhead line of the water stripper column and with a bottoms line of the water stripper column.

A third embodiment of the invention is a process for separating methanol from an initial mixture of oxygenates including water, methanol and at least one other oxygenate comprising, the process comprising separating water from the initial mixture to provide a water lean mixture comprising methanol and the at least one other oxygenate; adding water to the water depleted mixture comprising methanol and the at least one other oxygenate to provide a water enriched mixture; extracting methanol and water from the at least one other oxygenate in the water enriched mixture. An embodiment of the invention is one, any or all of prior embodiments in this paragraph up through the third embodiment in this paragraph further comprising separating dimethyl ether from the water lean mixture. An embodiment of the invention is one, any or all of prior embodiments in this paragraph up through the third embodiment in this paragraph wherein the water added to the water lean mixture is taken from the water separated from the initial mixture.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for separating methanol from other oxygenates comprising:
   separating water from a stream comprising water, methanol and at least one other oxygenate to provide a water rich stream and a methanol and oxygenate rich stream, said other oxygenate comprising at least one of acetaldehyde, acetone and methyl ethyl ketone;
   feeding said methanol and oxygenate rich stream and water to an extractive distillation column to provide an oxygenate rich stream and a methanol and water extract stream.

2. The process of claim 1 wherein the at least one other oxygenate includes dimethyl ether and further comprising separating dimethyl ether from said oxygenate rich stream to provide a dimethyl ether rich stream and a dimethyl ether lean, methanol and oxygenate rich stream and feeding said DME lean, methanol and oxygenate rich stream to said extractive distillation column.

3. The process of claim 2 further comprising feeding said dimethyl ether rich stream to an oxygenate conversion reactor.

4. The process of claim 1 wherein said water, fed to the extractive distillation column, is taken from said water rich stream.

5. The process of claim 1 further comprising separating methanol from said water to provide a water rich stream and a methanol rich stream.

6. The process of claim 4 further comprising feeding said methanol rich stream to an oxygenate conversion reactor.

7. The process of claim 1 wherein said stream comprising water, methanol and at least one other oxygenate and said methanol and oxygenate rich stream also include light hydrocarbons and further comprising separating said light hydrocarbons from said methanol and oxygenate rich stream.

8. The process of claim 1 wherein said stream comprising water, methanol and at least one other oxygenate and said oxygenate rich stream also include light hydrocarbons and further comprising separating said light hydrocarbons from said oxygenate rich stream.

9. The process of claim 1 wherein said water in the extractive distillation column increases the volatility of the other oxygenates relative to methanol.

10. The process of claim 1 wherein said stream comprising water, methanol and at least one other oxygenate is provided by a product separator column bottoms stream.

11. The process of claim 1 wherein said stream comprising water, methanol and at least one other oxygenate is provided by an oxygenate absorber column bottoms stream.

12. A process for separating methanol from an initial mixture of oxygenates including water, methanol and at least one other oxygenate comprising, said process comprising:
   separating water from said initial mixture to provide a water lean mixture comprising methanol and said at least one other oxygenate, said other oxygenate comprising at least one of acetaldehyde, acetone and methyl ethyl ketone;
   adding water to said water depleted mixture comprising methanol and said at least one other oxygenate to provide a water enriched mixture;
   extracting methanol and water from said at least one other oxygenate in said water enriched mixture.

13. The process of claim 12 wherein the at least one other oxygenate includes dimethyl ether and further comprising separating dimethyl ether from said water lean mixture.

14. The process of claim 12 wherein said water added to said water lean mixture is taken from the water separated from said initial mixture.

* * * * *